(12) United States Patent
Boehlen et al.

(10) Patent No.: US 9,314,317 B2
(45) Date of Patent: Apr. 19, 2016

(54) ABUTMENT FOR A DENTAL IMPLANT

(71) Applicants: Straumann Holding AG, Basel (CH); Ivoclar Vivadent AG, Schaan (LI)

(72) Inventors: Reto Boehlen, Gerzensee (CH); Markus Heinz, Naturns (IT); Georg Gorfer, Naturns (IT); Marcel Schweiger, Chur (CH)

(73) Assignees: Straumann Holding AG, Basel (CH); Ivoclar Vivadent AG, Schaan (LI)

( * ) Notice: Subject to any disclaimer, the term of this patent is extended or adjusted under 35 U.S.C. 154(b) by 105 days.

(21) Appl. No.: 13/892,762

(22) Filed: May 13, 2013

(65) Prior Publication Data

US 2013/0252204 A1 Sep. 26, 2013

Related U.S. Application Data

(63) Continuation of application No. 13/146,508, filed as application No. PCT/EP2010/000740 on Feb. 5, 2010, now abandoned.

(30) Foreign Application Priority Data

Feb. 5, 2009 (EP) ..................................... 09405021

(51) Int. Cl.
*A61C 13/225* (2006.01)
*A61C 8/00* (2006.01)

(52) U.S. Cl.
CPC ............... *A61C 8/0066* (2013.01); *A61C 8/005* (2013.01); *A61C 8/0054* (2013.01)

(58) Field of Classification Search
CPC .... A61C 8/0059; A61C 8/006; A61C 8/0062; A61C 8/0066; A61C 8/005; A61C 8/0054

USPC .......................................... 433/167, 172–176
See application file for complete search history.

(56) References Cited

U.S. PATENT DOCUMENTS

| 5,281,140 A | 1/1994 | Niznick |
| 5,823,776 A | 10/1998 | Duerr et al. |

(Continued)

FOREIGN PATENT DOCUMENTS

| CA | 2596988 | 8/2006 |
| DE | 102006005667 A1 | 1/2006 |

(Continued)

OTHER PUBLICATIONS

International Search Report mailed May 17, 2010 in PCT/2010/000740.

*Primary Examiner* — Heidi M Eide
(74) *Attorney, Agent, or Firm* — Therese A. Hendricks, Esq.

(57) ABSTRACT

Abutment for a dental implant (50), with an apical end (4) and with a coronal end (6) arranged opposite the apical end in the longitudinal direction. In the area of the apical end (4), the abutment has an insert portion (8) which is designed to be received by an opening of the dental implant and which has an anti-rotation segment (10) with at least one anti-rotation element (27) which is designed to cooperate with a corresponding mating anti-rotation element (53) of the dental implant (50). The anti-rotation element (27) has a groove (18', 18") which, from the edge of the anti-rotation segment (10) directed toward the apical end (4), extends in the coronal longitudinal direction along a groove portion (14) with a substantially constant groove width. The groove (18', 18") is continuously widened in a transition portion (20) adjoining the groove portion (14), in order to merge into a bevel (24', 24") in a bevel portion (22) adjoining the transition portion (20).

19 Claims, 16 Drawing Sheets

(56) References Cited

U.S. PATENT DOCUMENTS

| | | | |
|---|---|---|---|
| 5,873,722 A * | 2/1999 | Lazzara et al. | 433/173 |
| 6,227,859 B1 | 5/2001 | Sutter | |
| 7,104,797 B2 * | 9/2006 | Rassoli | 433/173 |
| 7,108,510 B2 * | 9/2006 | Niznick | 433/173 |
| 7,309,231 B2 * | 12/2007 | Engman | 433/173 |
| 7,484,959 B2 * | 2/2009 | Porter et al. | 433/173 |
| 2005/0065525 A1 * | 3/2005 | Aringskog et al. | 606/72 |
| 2006/0141418 A1 * | 6/2006 | Heo | 433/173 |
| 2007/0148620 A1 | 6/2007 | Kim | |
| 2008/0057476 A1 * | 3/2008 | Zettler et al. | 433/173 |
| 2008/0182227 A1 * | 7/2008 | Wolf et al. | 433/174 |
| 2009/0023110 A1 * | 1/2009 | Scherberger | 433/174 |

FOREIGN PATENT DOCUMENTS

| | | |
|---|---|---|
| EP | 1728486 A1 | 6/2006 |
| WO | WO 98/52488 A1 | 5/1998 |
| WO | WO 2004/080328 A1 | 9/2004 |

* cited by examiner

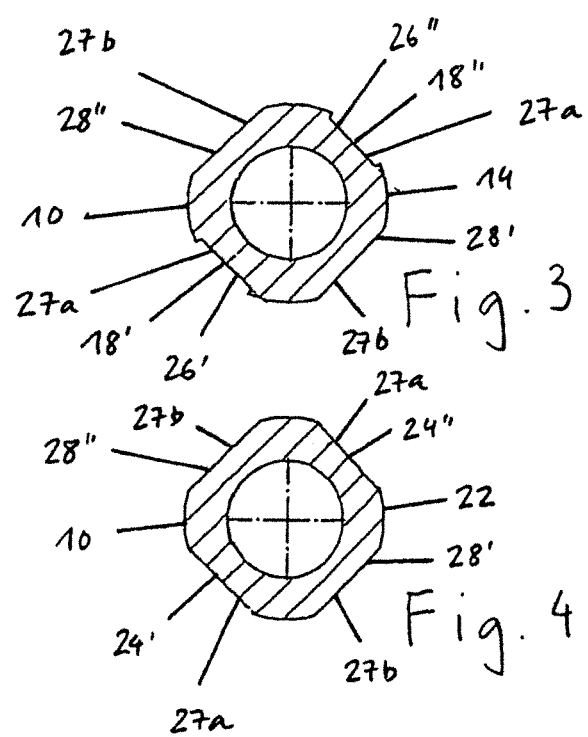

ABUTMENT FOR A DENTAL IMPLANT

FIELD OF THE INVENTION

The present invention relates to an abutment for a dental implant, a dental implant and a dental implant system comprising the abutment and the dental implant.

BACKGROUND

Two-part or multi-part dental implant systems are well known in the field of dental implantology. Such systems generally comprise a dental implant which has an outer thread and which is designed to be anchored in the bone of the patient, and an abutment (also called a secondary part) which serves as a base for the prosthetic structure. The abutment is often fitted in a corresponding coronal opening of the dental implant, i.e. an opening directed toward the crown of the tooth in the implanted state.

A problem that often arises in multi-part dental implant systems of this kind concerns the correct positioning of the abutment in the dental implant. This problem has been considered in the following prior art documents, for example:

U.S. Pat. No. 5,281,140 discloses a two-part abutment. The latter comprises a first part, which at its lower end is designed to be fitted in a complementary opening of the dental implant, and which at its upper end has a projection with a multiplicity of side faces, in order to be received in a complementary opening of a second part of the abutment.

However, mainly because of the relatively large number of individual parts, the solution described in said document has disadvantages as regards the sterility and stability of the connection between the abutment and the dental implant.

Proceeding from this, EP-A-1728486 proposed an abutment for use in a dental implant system that has means for guiding and locking the abutment in the dental implant. Said means comprise an area with anti-rotation means. These anti-rotation means comprise a surface which extends radially with respect to the axis of the abutment and which is designed to cooperate with the dental implant in such a way that the abutment is guided during insertion into the dental implant.

Moreover, CA-A-2596988 describes an abutment which, in its apical area, has a groove which forms an indexing element for defining the rotation position with respect to the dental implant.

The solution described in EP-A-1728486 and the solution described in CA-A-2596988 are both directed to a conventional dental implant system on the basis of metals, e.g. titanium. However, in a connection according to said documents, the material of the dental implant system is subjected to relatively high stress, such that, particularly in dental implant systems that comprise a ceramic material, for example zirconium oxide, the problem is that the dental implant system may be damaged. This is especially the case when the forces acting on the dental implant system act obliquely with respect to the axis thereof.

SUMMARY OF THE INVENTION

The object of the present invention is therefore to make available an abutment which can be connected to a corresponding dental implant in a manner secure against rotation and which at the same time ensures that the material stressing of the dental implant system can be kept relatively low, even when it is subjected to forces acting obliquely with respect to its axis.

The abutment of the present invention has an apical end, i.e. an end directed toward the bone in the implanted state of the dental implant system, and a coronal end arranged opposite the apical end in the longitudinal direction, i.e. an end directed toward the crown of the tooth in the implanted state of the dental implant system. In the area of the apical end, the abutment has an insert portion which is designed to be received by an opening of the dental implant. This insert portion has an anti-rotation segment comprising at least one anti-rotation element which is designed to cooperate with a corresponding mating anti-rotation element of the dental implant and thereby ensure anti-rotation between abutment and dental implant.

The anti-rotation element comprises a groove which, from the edge of the anti-rotation segment directed toward the apical end, extends in the coronal longitudinal direction along a groove portion with a substantially constant groove width. According to the invention, the groove is continuously widened in a transition portion adjoining the groove portion, and it merges into a bevel in a bevel portion adjoining the transition portion. The groove generally has a constant cross section in the groove portion. Thus, in the preferred rectangular groove cross section, the groove, in addition to having a constant groove width, also has a constant groove depth.

In the context of the present invention, a bevel is understood as meaning a flat surface having no side faces, as is obtained, for example, on milling a cylindrical body. Since the anti-rotation segment of the abutment according to the invention generally has a circular cylindrical basic shape, the bevel describes, in cross section, a straight line connecting the arc-shaped portions of the adjacent circular cylindrical jacket portions. The plane of the bevel generally extends parallel to the longitudinal direction of the abutment or of the anti-rotation segment thereof.

The configuration according to the invention now allows the abutment to be connected to the dental implant in a manner secure against rotation, such that the stresses acting on the dental implant system are distributed optimally, as a result of which the material stressing is kept low and a high degree of stability of the dental implant system is achieved.

The groove of the present invention has, in addition to the bottom face, two side faces. These form additional abutment faces of the anti-rotation element and ensure that anti-rotation is achieved with substantially less play than would be the case with a mere bevel.

Generally speaking, the anti-rotation mating element of the dental implant is a projection directed toward the interior of the opening of the dental implant. This projection is preferably in the form of a rail extending in the longitudinal or axial direction.

The groove width in the groove portion is preferably such that the side faces of the groove bear at least approximately directly on the respective side face of the projection.

In order to design the abutment as simply as possible and make it compatible with a large number of dental implants, at least the groove portion preferably has a cylindrical shape.

It is also preferable, for achieving the simplest possible design, that the bottom face of the groove and the bevel lie in the same plane. This permits a very simple and extremely stable anti-rotation.

It is also preferable that the continuous widening of the groove width in the transition portion is effected substantially symmetrically, as a result of which an optimal reduction of the material stressing is achieved.

It was found that, according to another preferred embodiment, the bevel of the abutment according to the invention is not formed as far as the edge of the anti-rotation segment directed toward the coronal end, which further ensures a high degree of stability of the connection between abutment and dental implant. Therefore, by virtue of its generally circular cylindrical basic shape, the anti-rotation segment in this embodiment also has a circular cylindrical shape in its edge area directed toward the coronal end.

The anti-rotation segment of the abutment according to the invention generally comprises more than one anti-rotation element, preferably two or four anti-rotation elements. It is particularly preferable that two grooves are arranged lying diametrically opposite each other and, between them, additional bevels lying diametrically opposite each other are arranged as additional anti-rotation elements. As is shown in connection with the figures, it was surprisingly found that, in a dental implant system comprising an abutment according to this preferred embodiment, the maximum material stressing is considerably less than in a dental implant system with an abutment not according to the invention. It was also found that the maximum stressing of the anti-rotation segment lies in the area between the anti-rotation elements in the abutment according to the invention, whereas it lies within the area of an anti-rotation element in the case of an abutment not according to the invention. This also contributes decisively to the increased stability of the dental implant system achieved according to the invention.

Generally speaking, the abutment is secured on the dental implant by means of a securing element. For this purpose, the abutment according to the invention generally has a recess which extends from the coronal end to the apical end and which is designed in such a way that it can receive the securing element. The recess preferably has a support face which protrudes radially in the direction toward the interior and which is designed to cooperate with a corresponding mating support face of the securing element. The support face is preferably conically shaped, which, when a corresponding conical mating support face of the securing element is present, ensures that the least possible play exists between abutment and securing element. The cone angle of the conical support face is preferably in the range of 20 to 40°, particularly preferably about 30°.

It has also been found that at least this conical support face advantageously has a surface roughness Ra (according to EN ISO 4287) in the range of 0.1 to 0.15. In this range of surface roughness, sufficient coefficients of friction are ensured between the support faces of the parts that are to be connected, and the play between these parts can be kept relatively low, which results in a high degree of fatigue resistance.

In addition to the described abutment, the present invention also relates to a dental implant with an opening for receiving the insert portion of the described abutment, the dental implant having at least one projection which protrudes into the interior of the opening, forms an anti-rotation mating element and is designed to cooperate with a corresponding anti-rotation element of the abutment. The invention further relates to a dental implant system comprising the abutment and the dental implant.

Although the advantages of the present invention mean that it is particularly suitable for a dental implant system comprising a ceramic material, the invention is of course also suitable for dental implant systems made of any other material suitable for dental implant systems, particularly a metal such as titanium, zirconium, gold, and any other material known by a person skilled in the art to be suitable.

BRIEF DESCRIPTION OF THE DRAWINGS

The invention is described in detail with reference to the attached figures, in which:

FIG. 3 shows the abutment according to FIG. 1, in cross section through the section plane III-III';

FIG. 4 shows the abutment according to FIG. 1, in cross section through the section plane IV-IV';

DETAILED DESCRIPTION

Figure 1:
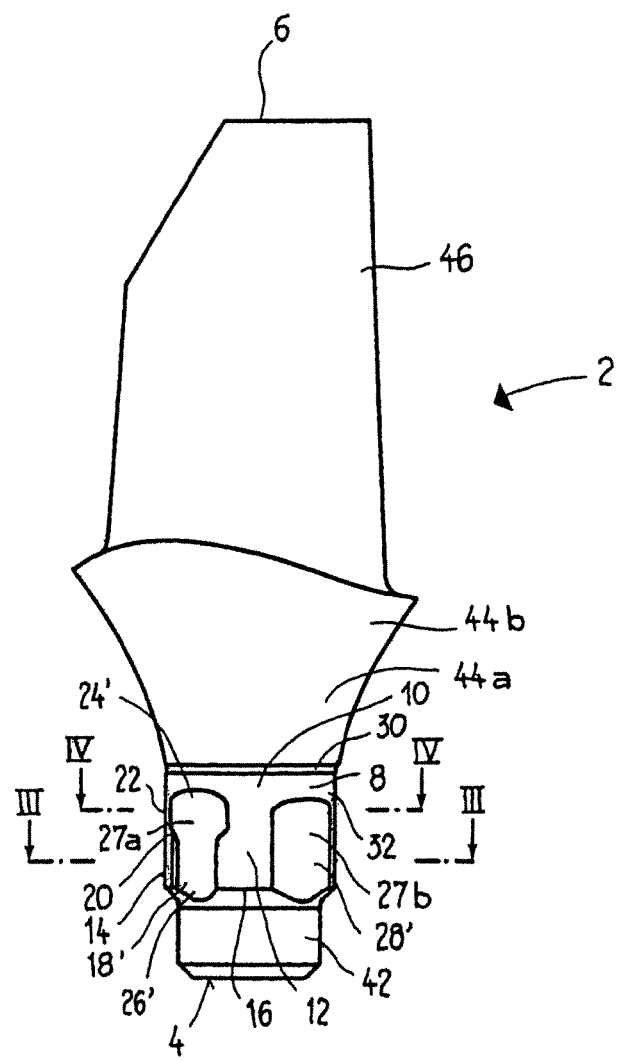
FIG. 1 shows a side view of a straight abutment according to the invention.
Figure 2:
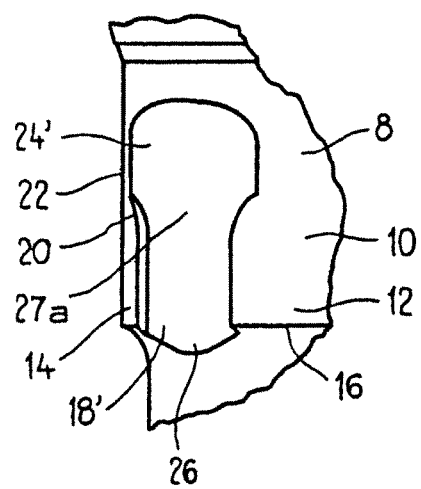
FIG. 2 shows an enlarged detail from FIG. 1, focusing on the anti-rotation element according to the invention.
Figure 5:
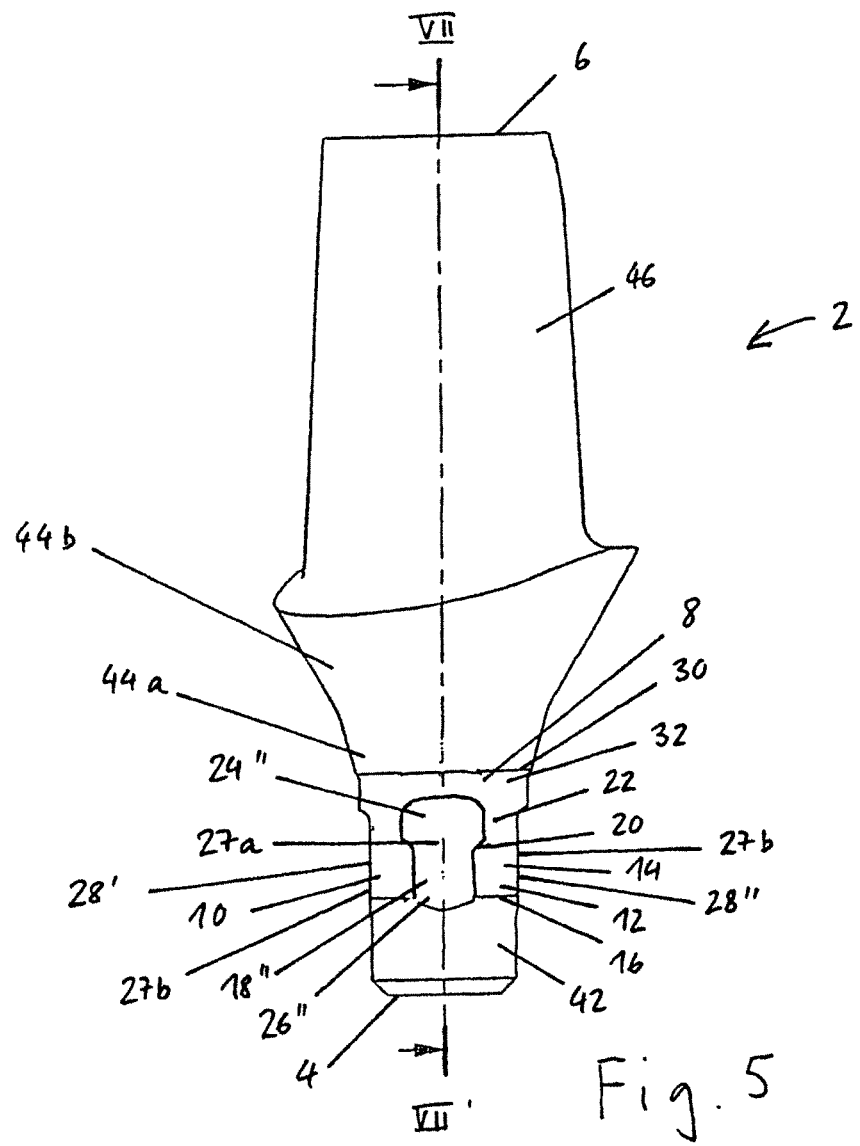
FIG. 5 shows another side view of the abutment according to FIG. 1, seen from a direction offset in the circumferential direction by ca. 135° about the axis in relation to FIG. 1.
Figure 6:
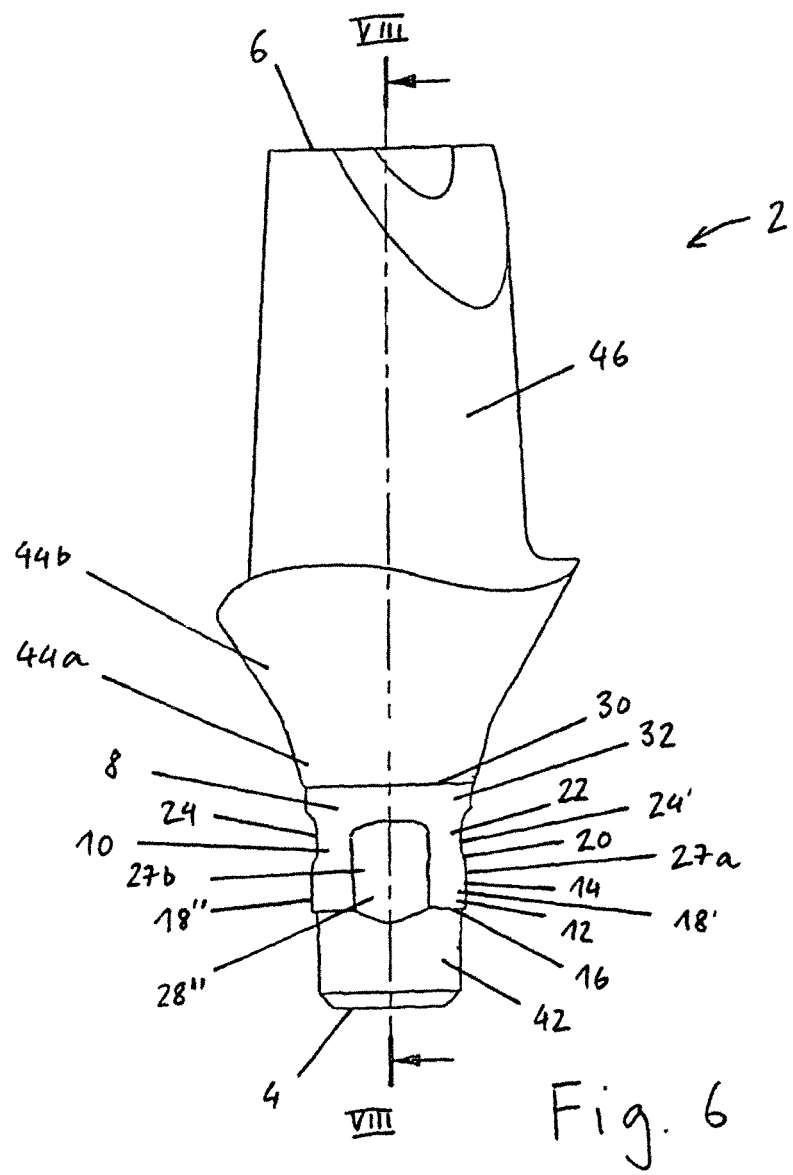
FIG. 6 shows another side view of the abutment according to FIG. 1, seen from a direction offset in the circumferential direction by ca. 90° about the axis in relation to FIG. 5.

As is clear in particular from FIGS. 1 and 5 to 8, the abutment 2 of the present invention has an apical end 4, i.e. an end directed toward the bone in the implanted state, and a coronal end 6 arranged opposite the apical end. In the area of the apical end 4, the abutment 2 has an insert portion 8 which is designed to be received in an opening of a dental implant. The insert portion 8 comprises an anti-rotation segment 10 which, in its edge area 12 directed toward the apical end, has a groove portion 14. In the embodiment shown in the figures, the groove portion 14 has two diametrically opposite grooves 18', 18'' which extend in the longitudinal direction from the apical edge 16 of the anti-rotation segment 10 and are of substantially constant cross section, as can be seen from FIG. 3, for example. The groove portion 14 is adjoined in the coronal direction by a transition portion 20 in which the width of the groove 18', 18" is continuously widened in order to merge into a bevel 24', 24" lying in a beveled portion 22 adjoining the transition portion 20. In the embodiment shown, the bottom face 26', 26" of the groove 18', 18" and the bevel 24', 24" lie in the same plane. In the embodiment shown, the widening of the width of the groove 18', 18" in the transition portion 20 is effected symmetrically, specifically such that the groove 18', 18" has a goblet-shaped profile. The groove forms, with the adjoining bevel, an anti-rotation element 27a.

Two additional bevels 28', 28", likewise lying diametrically opposite each other, are arranged between the grooves 18', 18" and extend in the longitudinal direction from the apical edge 16 of the anti-rotation segment and each form an additional anti-rotation element 27b. These additional bevels 28', 28" extend slightly less far in the longitudinal direction than the bevels 24', 24" adjoining the grooves. In the embodiment shown, neither the bevels 28', 28" arranged between the grooves 18', 18" nor the bevels 24', 24" adjoining the grooves are formed as far as the edge 30 of the anti-rotation segment 10 directed toward the coronal end 6. As can be seen in particular from FIGS. 7 and 8, the transition from the bevels 24', 24" or 28', 28" into the edge area 32 directed toward the coronal end is arc-shaped in longitudinal section. Said coronal edge area 32 has a circular cylindrical shape.

In the embodiment shown, the ratio of the extent of the groove portion 14 in the longitudinal direction to the extent of the transition portion 20 in the longitudinal direction is ca. 2:1, and the ratio of the extent of the groove portion 14 in the longitudinal direction to the extent of the bevel portion 22 in the longitudinal direction is ca. 1:1. However, every other ratio suitable for the purposes of the present invention is also conceivable.

Figure 7:
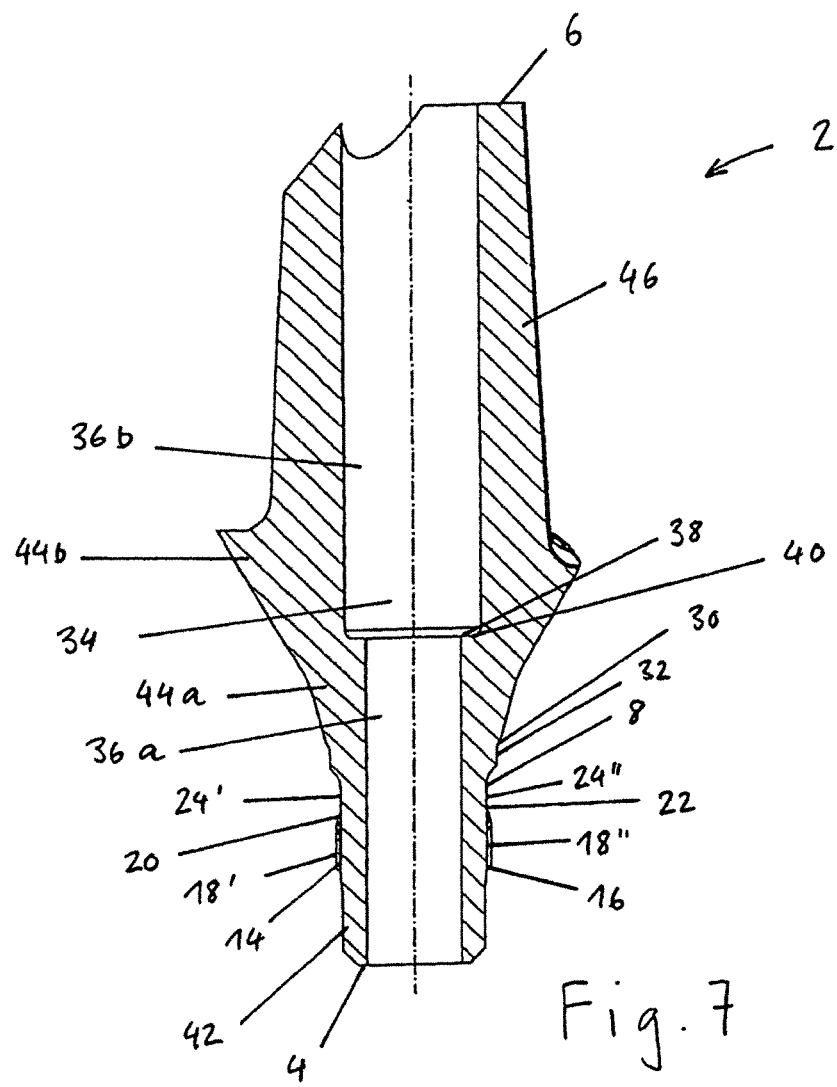
FIG. 7 shows a longitudinal section through the abutment according to FIGS. 1, 5 and 6, through the section plane VII-VII'.
Figure 8:
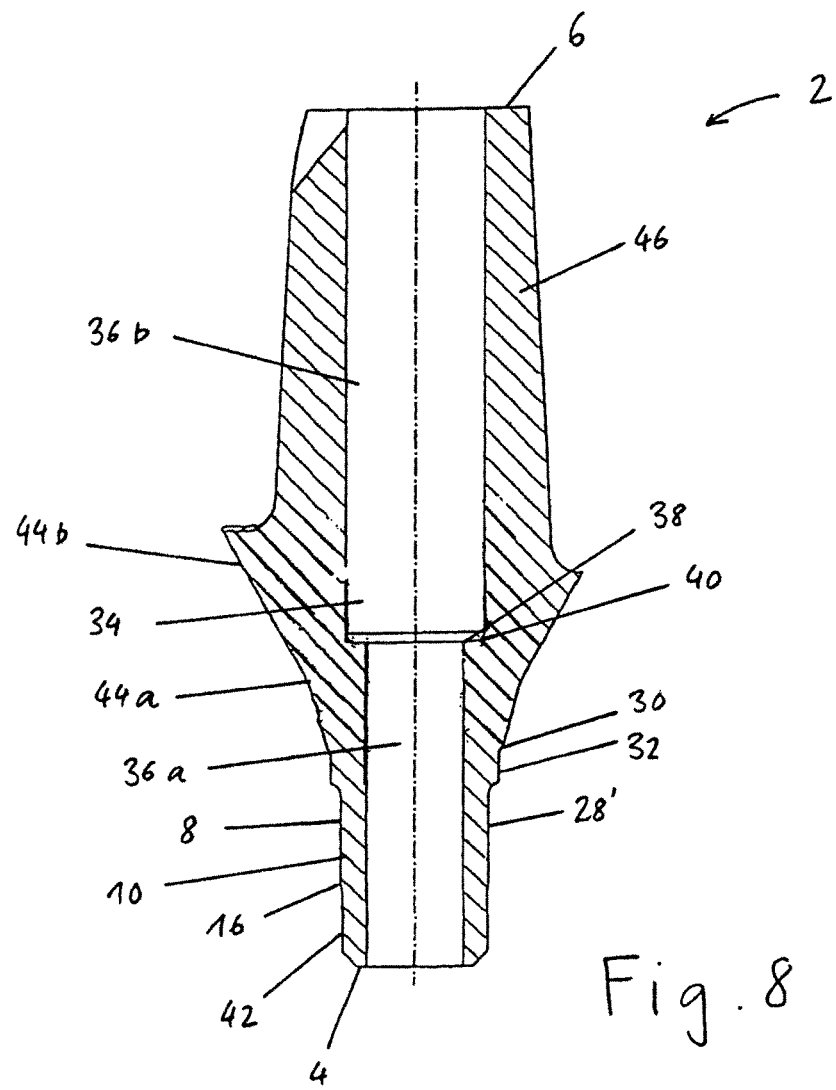
FIG. 8 shows a longitudinal section through the abutment according to FIGS. 1, 5 and 6, through the section plane VIII-VIII'.

As can be seen in particular from FIGS. 7 and 8, the abutment 2 has a recess 34 which extends from the coronal end 6 to the apical end 4. This recess 34 comprises a first recess portion 36a directed toward the apical end 4 and a second recess portion 36b directed toward the coronal end 6. Between the first recess portion 36a and the second recess portion 36b, the recess 34 has a projection 38, which protrudes radially in the direction toward the interior and which forms a support face 40 designed to cooperate with a corresponding mating support face of the securing element. In the embodiment shown, the support face 40 lies in a plane extending at right angles to the longitudinal axis. However, it is also conceivable in particular for the support face to be shaped conically.

As is clear in particular from FIGS. 1 and 5 to 8, the anti-rotation segment 10 is adjoined in the apical direction by a circular cylindrical insertion portion 42, which has a smaller diameter than the anti-rotation segment 10 and whose edges are rounded. Arranged in the coronal direction toward the anti-rotation segment 10 there is a conically widening first shoulder portion 44a, which merges into a likewise conically widening second shoulder portion 44b whose cone angle is greater than that of the first shoulder portion 44a.

Figure 9:
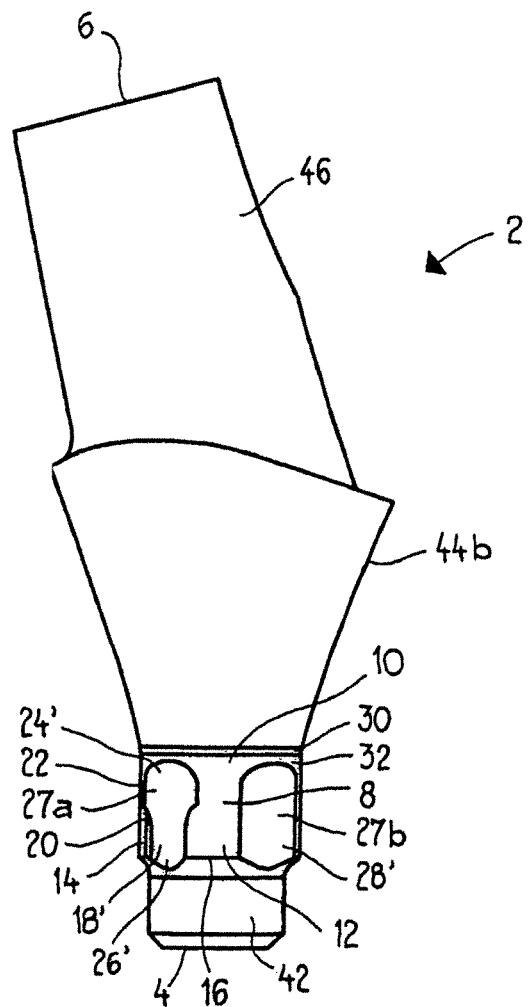
FIG. 9 shows a side view of an angled abutment according to the invention.

The embodiment shown in FIG. 9 differs from that in FIGS. 1 to 8 primarily in that the abutment portion 46 adjoining the second shoulder portion 44b in the coronal direction is oblique with respect to the longitudinal axis. Moreover, the different orientation of the abutment portion 46 according to FIG. 9 is accounted for by the bevels 24', 28' extending further in the coronal direction than according to FIGS. 1 to 8.

Figure 10:
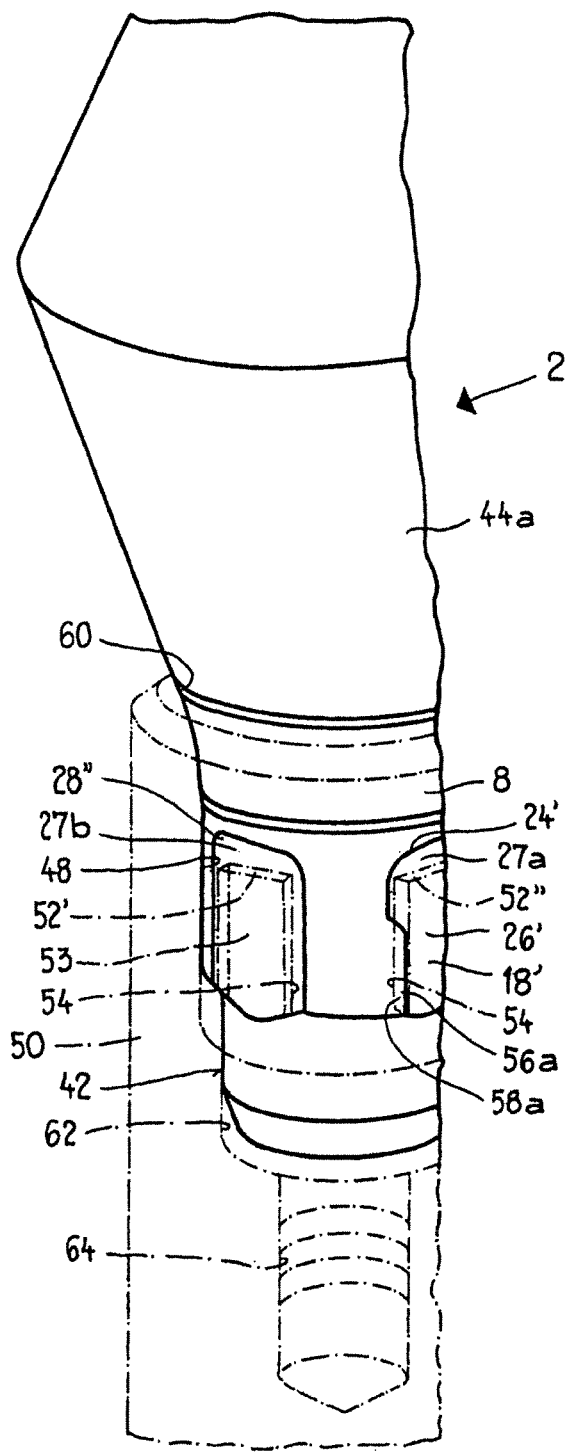
FIG. 10 shows a perspective view of a portion of an abutment according to the invention, which is connected to a symbolically indicated dental implant.
Figure 11:
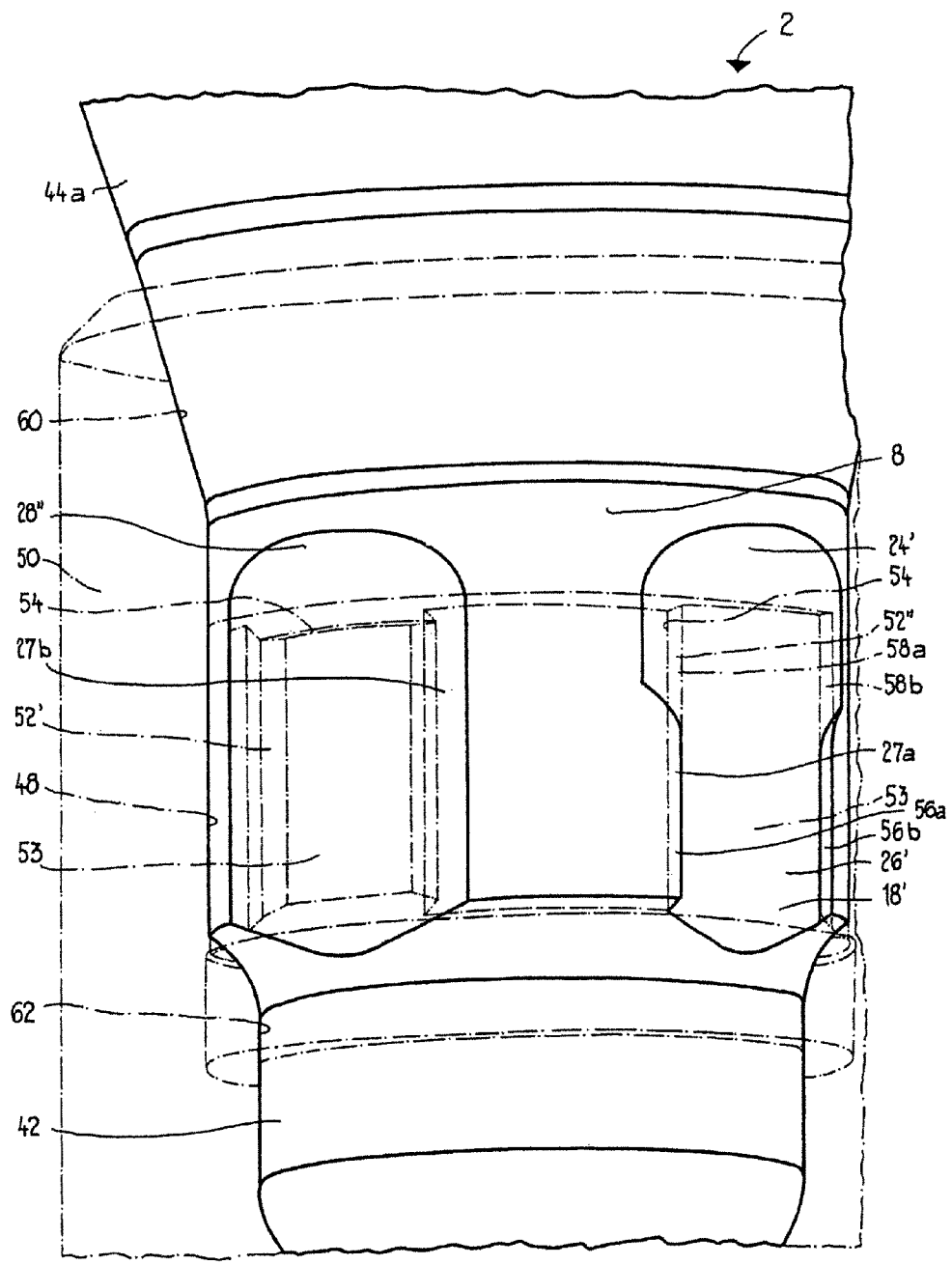
FIG. 11 shows a detail, from another perspective, of the anti-rotation segment of the abutment according to FIG. 10 connected to the dental implant.
Figure 12:
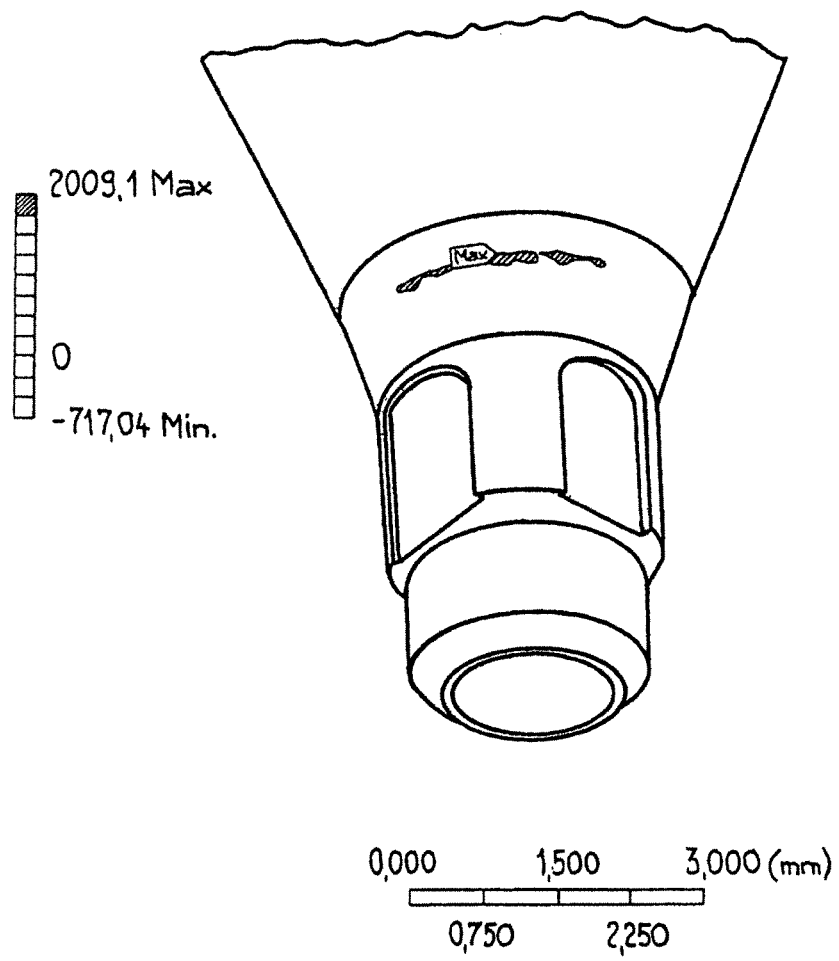
FIG. 12 shows a perspective view of a portion of an abutment according to a comparison example, in which view the maximum local material stress in the shoulder portion under a defined force is indicated.
Figure 13:
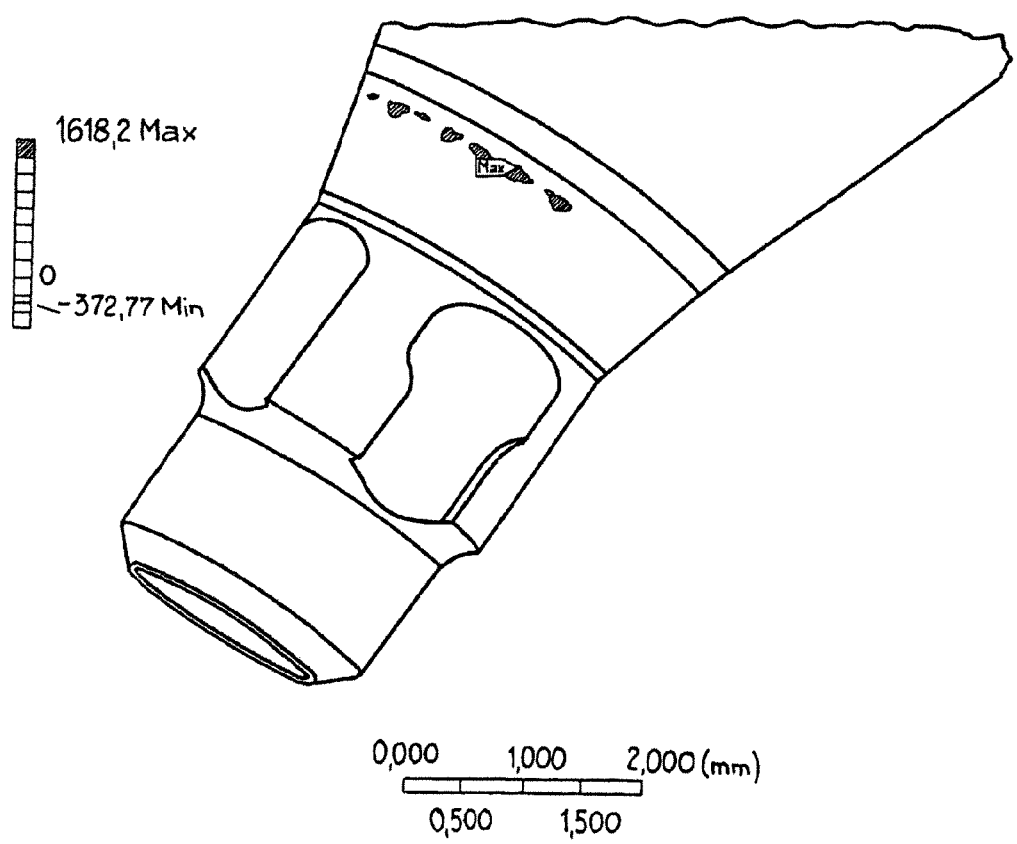
FIG. 13 shows a perspective view of a portion of an abutment according to the invention, which is connected to a symbolically indicated dental implant, in which view the maximum local material stress in the shoulder portion under a defined force is indicated.
Figure 14:
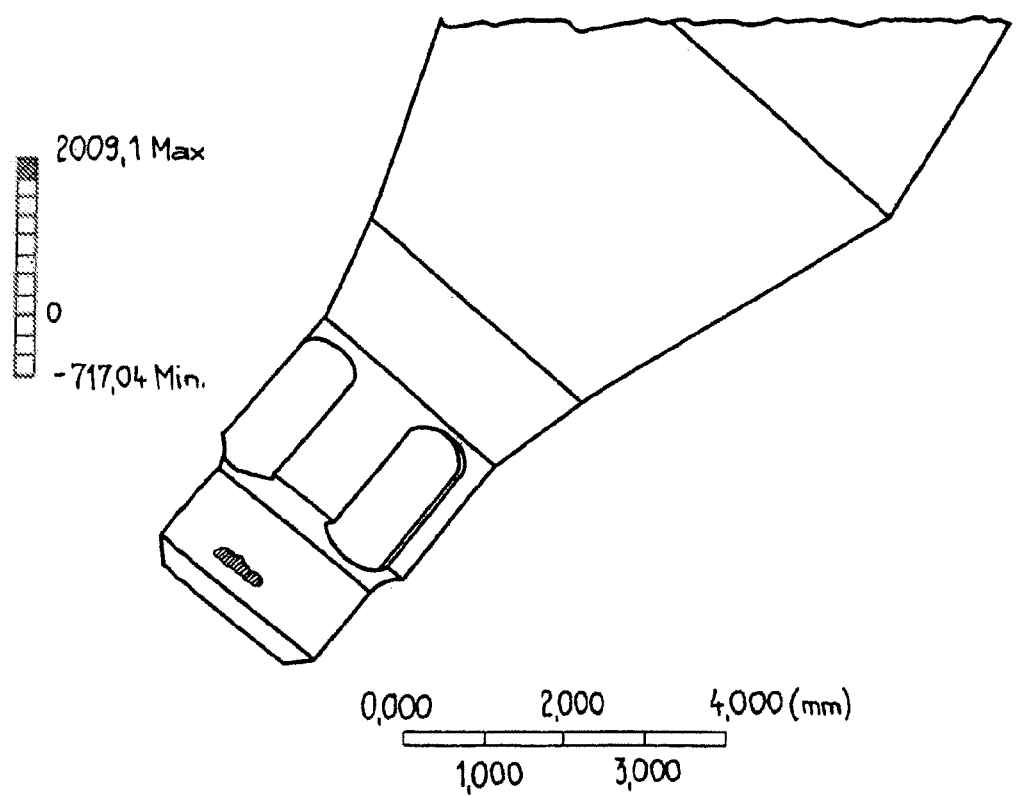
FIG. 14 shows a perspective view of a portion of an abutment according to the comparison example in FIG. 12, in which view the maximum local material stress in the apical insertion portion under a defined force is indicated.
Figure 15:
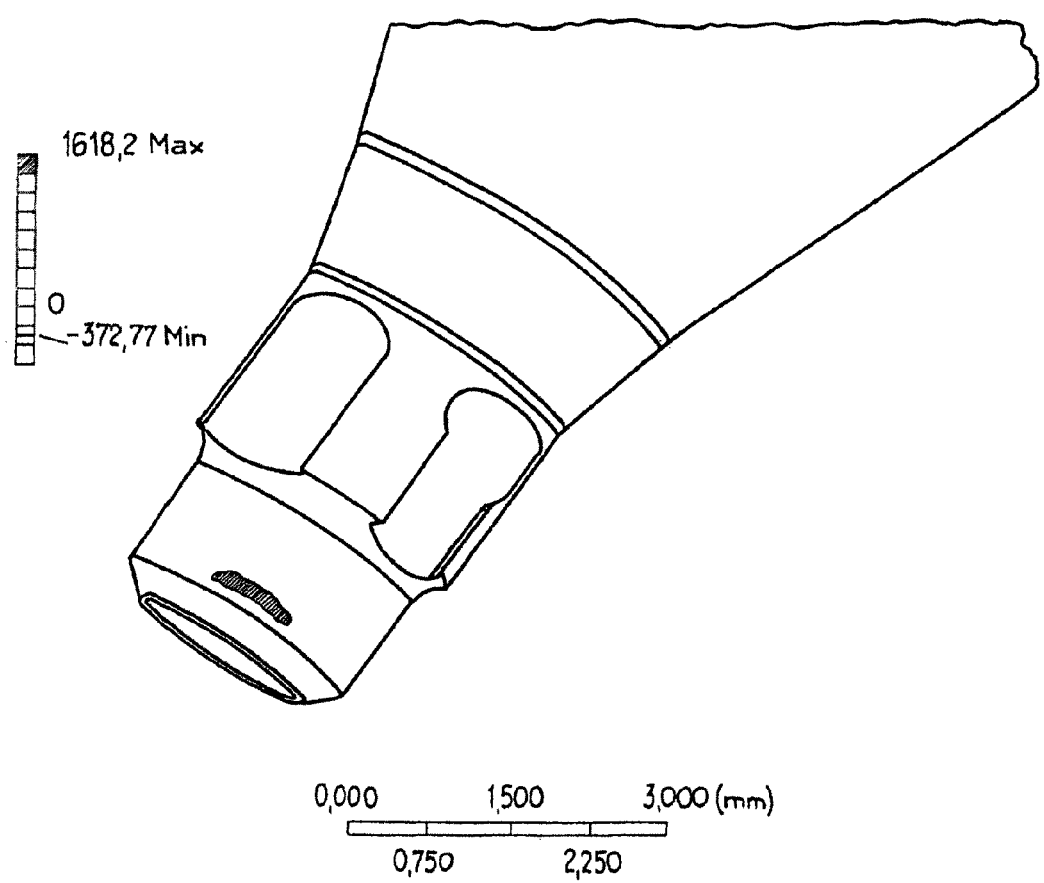
FIG. 15 shows a perspective view of a portion of the abutment according to the invention in FIG. 13, in which view the maximum local material stress in the apical insertion portion under a defined force is indicated.

As can be seen in particular from FIGS. 10 and 11, the abutment 2, or the insert portion 8 thereof, is inserted into a complementary coronal opening 48 of the dental implant 50. In the embodiment shown, the dental implant 50 has four projections, of which two (52', 52") are shown and which cooperate, as anti-rotation mating element 53, with the respective anti-rotation element 27a, 27b of the abutment 2. The surface 54 of the projections 52', 52" bears at least approximately directly on the bevel 28" or the groove bottom face 26' and the adjacent bevel 24' of the respective anti-rotation element 27b or 27a. On the anti-rotation element 27a comprising the groove 18', the side faces 56a, 56b of the groove 18' bear at least approximately directly on the respective side face 58a, 58b of the projection 52".

Corresponding to the first shoulder portion 44a of the abutment part 2, the internal edge area 60 of the opening 48, on which edge area the shoulder portion bears, is likewise conical in shape.

The area of the coronal opening 48 comprising the projections 52', 52" is adjoined in the apical direction by a substantially circular cylindrical opening portion 62, in which the circular cylindrical insertion portion 42 of the abutment 2 is received. In the apical direction from this circular cylindrical opening portion 62 there is an inner thread portion 64, which is designed to cooperate with a corresponding outer thread of a securing element (not shown) for securing the abutment 2 on the dental implant 50, as can be seen in particular from FIG. 10.

The material stressing of the abutment, determined at a defined force acting at an angle of 30° with respect to the longitudinal axis, is shown in FIGS. 12 to 17. Here, according to FIGS. 13 and 15, for the abutment of the present invention, a maximum stress defined as 100% is established in the shoulder portion or in the insertion portion, which maximum stress is substantially below the stress of 124% in the corresponding portions in the comparison example according to FIGS. 12 and 14.

Figure 16:
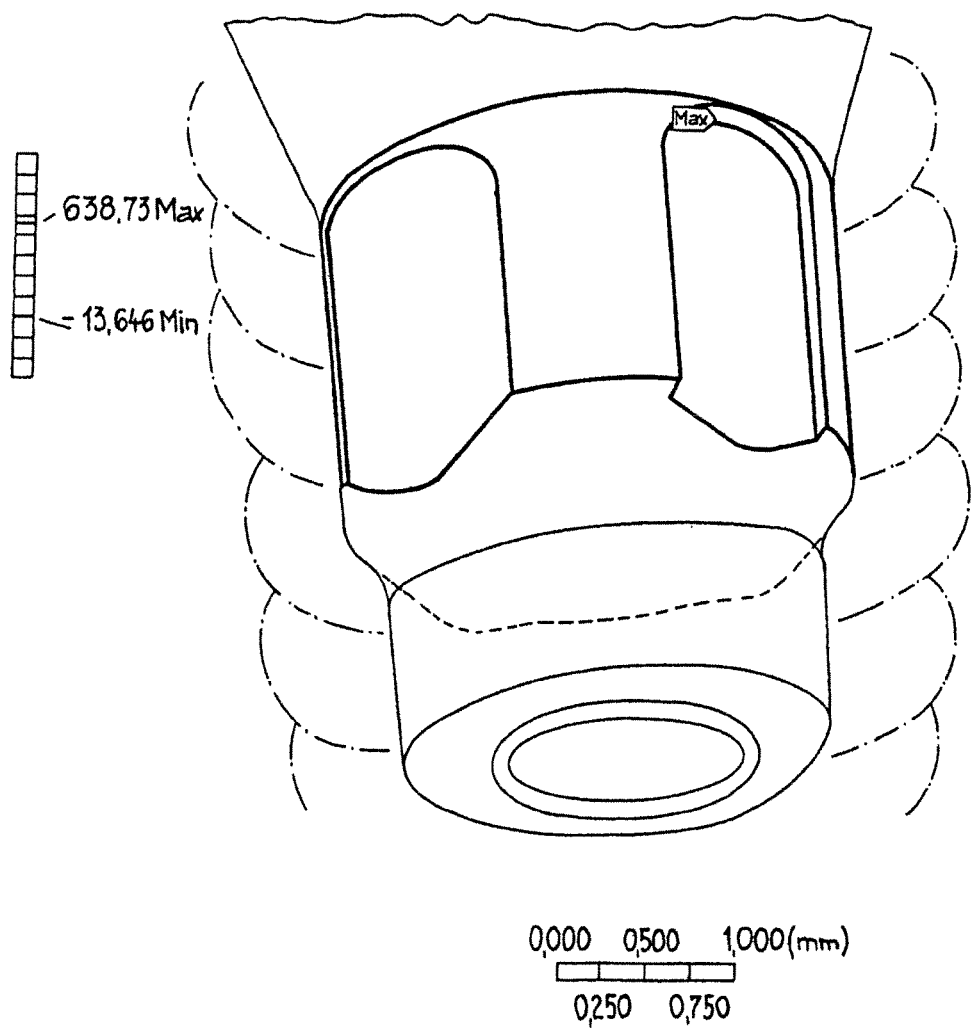
FIG. 16 shows a perspective view of the anti-rotation segment of the abutment according to the comparison example in FIG. 12, in which view the maximum local material stress under a defined force is indicated.
Figure 17:
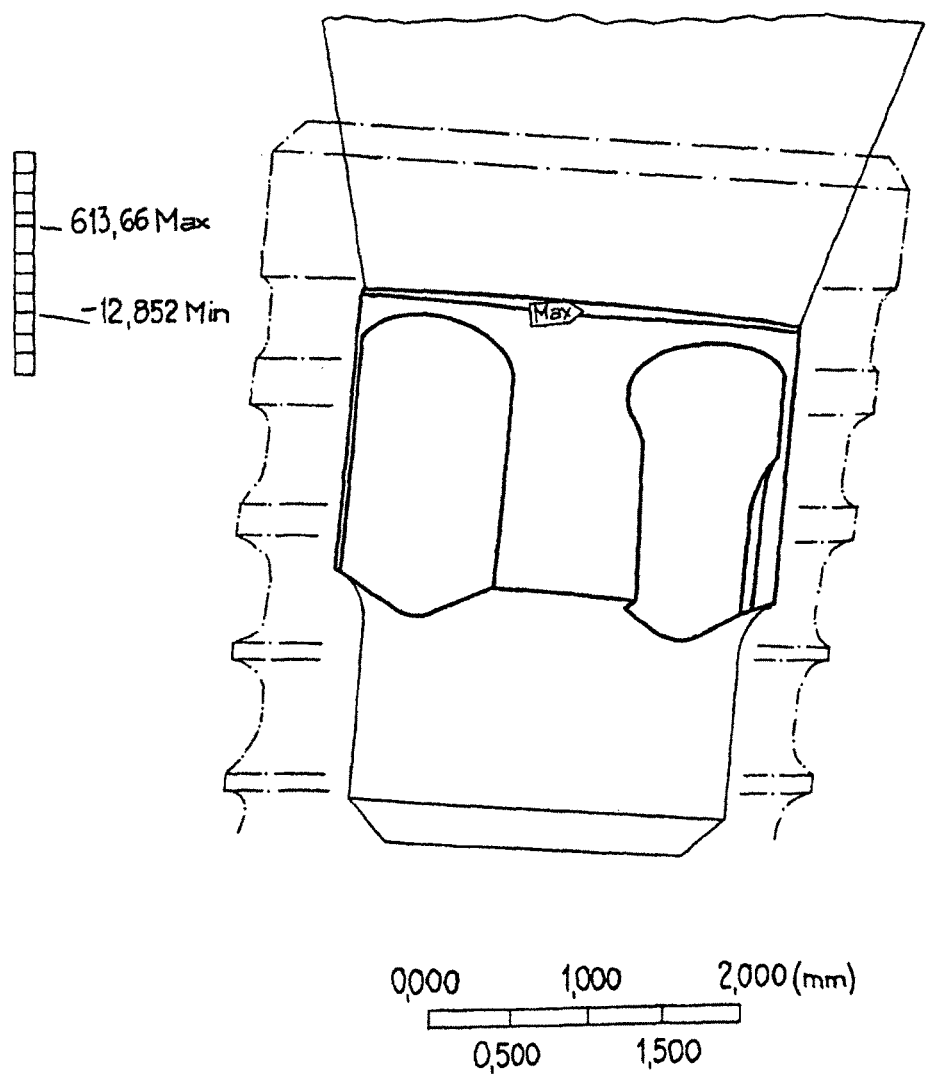
FIG. 17 shows a perspective view of the anti-rotation segment of the abutment according to the invention in FIG. 13, in which view the maximum local material stress under a defined force is indicated.

According to FIG. 17, compared to FIG. 16, the maximum material stress in the anti-rotation segment has a value of 37.9% and is much lower than the material stress in the comparison example (39.5%). Moreover, FIG. 17 shows that the maximum material stress is in the coronal edge area of the anti-rotation segment and not in the area of the anti-rotation element, as is the case in the comparison example shown in FIG. 16.

For reasons of clarity, a relatively high force of 500 N was assumed for the material stress shown in FIGS. 12 to 17, with a concrete value of 1618.2 MPa being obtained for the stress defined as 100%. Analogous differences in material stress between the abutments according to the invention and those not according to the invention are also obtained, albeit at substantially lower values, at a force of 240 N, which is customary for such tests.

The invention claimed is:

1. An abutment for a dental implant, the abutment comprising an apical end and with a coronal end arranged opposite the apical end in the longitudinal direction, which abutment has, in the area of the apical end, an insert portion which is designed to be received by an opening of the dental implant and which has an anti-rotation segment comprising at least one anti-rotation element which is designed to cooperate with a corresponding mating anti-rotation element of the dental implant, the anti-rotation element comprising a groove having a bottom surface between opposing side faces, the groove having a groove portion extending in the coronal direction from an apical edge of the anti-rotation segment directed toward the apical end with a substantially constant groove width between the opposing side faces of the groove, and wherein the groove is continuously widened in a transition portion adjoining the groove portion, in order to merge into a flat bottom surfaced bevel area having no side faces coronally adjoining the transition portion.

2. The abutment as claimed in claim 1, wherein the anti-rotation element is designed to cooperate with a corresponding projection having opposing side faces and directed toward the interior of the opening of the dental implant.

3. The abutment as claimed in claim 2, wherein the groove width in the groove portion is such that the side faces of the groove bear approximately directly on the respective side faces of the projection.

4. The abutment as claimed in claim 1, wherein at least the groove portion has a cylindrical shape.

5. The abutment as claimed in claim 1, wherein the bottom face of the groove and the bevel lie in the same plane.

6. The abutment as claimed in claim 1, wherein the bevel is not formed as far as a coronal edge portion of the anti-rotation segment directed toward the coronal end.

7. The abutment as claimed in claim 6, wherein the anti-rotation segment has a circular cylindrical shape in the coronal edge area directed toward the coronal end.

8. The abutment as claimed in claim 1, wherein the continuous widening of the groove in the transition portion is effected substantially symmetrically.

9. The abutment as claimed in claim 1, wherein the anti-rotation segment comprises up to four anti-rotation element.

10. The abutment as claimed in claim 9, wherein two anti-rotation elements are arranged lying diametrically opposite each other and, between the anti-rotation elements, additional bevels lying diametrically opposite each other are arranged as additional anti-rotation elements.

11. The abutment of claim 9, wherein the anti-rotation segment has two anti-rotation elements.

12. The abutment of claim 9, wherein the anti-rotation segment has four anti-rotation elements.

13. The abutment as claimed in claim 1, wherein the abutment has a recess which extends from the coronal end to the apical end and which is designed to receive a securing element, and the abutment has a conical support face which protrudes radially into the interior of the recess and which is designed to cooperate with a corresponding mating support face of the securing element.

14. The abutment as claimed in claim 13, wherein the conical support face has a cone angle in the range of 20 to 40°.

15. The abutment of claim 14, wherein the cone angle is about 30°.

16. A dental implant with an opening for receiving the insert portion of the abutment as claimed in claim 1, wherein the dental implant has at least one projection which protrudes into the opening and forms an anti-rotation mating element of the implant and which is designed to cooperate with a corresponding anti-rotation element of the abutment.

17. The dental implant as claimed in claim 16, wherein the projection extends in the longitudinal direction, and the projection has side faces designed to bear at least approximately directly on the respective side faces of the groove of the abutment.

18. A dental implant system comprising an abutment as claimed in claim 1, and a dental implant with an opening for receiving the insert portion of the abutment, wherein the dental implant has at least one projection having opposing side faces which protrudes into the opening and forms an anti-rotation mating element and which is designed to cooperate with a corresponding anti-rotation element of the abutment.

19. The dental implant system of claim 18, wherein the projection extends in the longitudinal direction, and the side faces of the projection are designed to bear at least approximately directly on the respective side faces of the groove of the abutment.

* * * * *

UNITED STATES PATENT AND TRADEMARK OFFICE
CERTIFICATE OF CORRECTION

PATENT NO. : 9,314,317 B2
APPLICATION NO. : 13/892762
DATED : April 19, 2016
INVENTOR(S) : Boehlen et al.

It is certified that error appears in the above-identified patent and that said Letters Patent is hereby corrected as shown below:

In the claims,

In column 7, line 28 (claim 9), delete "element" and replace with -- elements --

Signed and Sealed this
Twenty-first Day of June, 2016

Michelle K. Lee
*Director of the United States Patent and Trademark Office*